(12) United States Patent
Doi et al.

(10) Patent No.: US 11,166,888 B2
(45) Date of Patent: Nov. 9, 2021

(54) WATER-IN-OIL EMULSION COSMETIC

(71) Applicant: SHISEIDO COMPANY, LTD., Tokyo (JP)

(72) Inventors: Ryosuke Doi, Yokohama (JP); Hirohito Shirakami, Yokohama (JP); Takahiro Yamashita, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/641,527

(22) PCT Filed: Aug. 24, 2018

(86) PCT No.: PCT/JP2018/031309
§ 371 (c)(1),
(2) Date: Feb. 24, 2020

(87) PCT Pub. No.: WO2019/044685
PCT Pub. Date: Mar. 7, 2019

(65) Prior Publication Data
US 2020/0230036 A1 Jul. 23, 2020

(30) Foreign Application Priority Data

Aug. 31, 2017 (JP) ................ JP2017-167693

(51) Int. Cl.
| | |
|---|---|
| *A61K 8/64* | (2006.01) |
| *A61K 8/06* | (2006.01) |
| *A61K 8/04* | (2006.01) |
| *A61K 8/31* | (2006.01) |
| *A61K 8/37* | (2006.01) |
| *A61K 8/894* | (2006.01) |
| *A61K 8/895* | (2006.01) |
| *A61Q 5/00* | (2006.01) |

(52) U.S. Cl.
CPC .............. *A61K 8/064* (2013.01); *A61K 8/046* (2013.01); *A61K 8/31* (2013.01); *A61K 8/37* (2013.01); *A61K 8/894* (2013.01); *A61K 8/895* (2013.01); *A61Q 5/00* (2013.01); *A61K 2800/95* (2013.01)

(58) Field of Classification Search
CPC . A61K 8/064; A61K 8/37; A61K 8/31; A61K 2800/95; A61K 8/375; A61K 8/891; A61K 8/895; A61Q 5/00; A61Q 5/06
See application file for complete search history.

(56) References Cited

U.S. PATENT DOCUMENTS

| | | | |
|---|---|---|---|
| 5,412,004 A * | 5/1995 | Tachibana ................ | A61K 8/06 514/844 |
| 6,905,695 B1 * | 6/2005 | Afriat ...................... | A61K 8/02 424/400 |
| 2008/0311062 A1 * | 12/2008 | Dickinson .............. | A61K 8/898 424/70.1 |
| 2016/0175240 A1 * | 6/2016 | Tan ........................ | A61K 8/927 424/401 |

FOREIGN PATENT DOCUMENTS

| | | |
|---|---|---|
| JP | 64-79104 | 3/1989 |
| JP | 5-139929 | 6/1993 |
| JP | H 10-45546 | 2/1998 |
| JP | 2001-2521 | 1/2001 |
| JP | 2001-48737 | 2/2001 |
| JP | 2005-171146 | 6/2005 |
| JP | 2009-155274 | 7/2009 |
| JP | 2009-209103 | 9/2009 |
| JP | 2009209103 A * | 9/2009 |
| JP | 2009-242294 | 10/2009 |

OTHER PUBLICATIONS

Author: Marie; title: A Quick Guide to Candelilla Wax & Liquid Oil Ratios; Apr. 26, 2014. Downloaded from https://www.humblebeeandme.com/quick-guide-candelilla-wax-liquid-oil-ratios/ (Year: 2014).*

* cited by examiner

*Primary Examiner* — Yanzhi Zhang
(74) *Attorney, Agent, or Firm* — Andrew F. Young, Esq.; Nolte Lackenbach Siegel

(57) ABSTRACT

The purpose of the present invention is to provide a water-in-oil emulsion cosmetic that, while having an excellent hair-styling effect, exhibits a strong ability to moisturize the coated tissue, provides a smooth finger manipulation sense unlike that of a cream or wax, and does not produce stickiness on the hands and hair. The water-in-oil emulsion cosmetic according to the present invention is characterized by containing (A) a crosslinked siloxane elastomer, (B) a solid oil component, (C) a liquid oil component, and (D) at least 55 mass % water, wherein the ratio of component (B) to component (C) ((B)/(C)) is 0.25 to 1.5.

5 Claims, 2 Drawing Sheets

WATER-IN-OIL EMULSION COSMETIC

CROSS REFERENCE TO RELATED APPLICATIONS

This application relates to and claims priority as a § 371 national phase, from PCT/JP2018/031309 filed Aug. 24, 2018, the entire contents of which are incorporated herein by reference, which in turn claims priority from JP Ser. No.: 2017-167693 filed Aug. 31, 2017.

FIGURE SELECTED FOR PUBLICATION

FIG. 1

TECHNICAL FIELD

The present invention relates to a water-in-oil emulsion cosmetic. More specifically, the present invention relates to a solid or semi-solid cosmetic, particularly a cosmetic that provides excellent hairstyling effects and imparts moistness without causing stickiness, when applied to keratin fibers such as hair.

BACKGROUND ART

In general, hairstyling resins and oil components such as waxes are contained in hairstyling agents to achieve good hairstyle setting ability and keepability. However, in recent years, there has been a trend towards favoring hairstyles having a natural impression, without glossiness or shininess. Additionally, as for the texture, the user aspires non-sticky cosmetics.

For example, Patent Document 1 proposes a hairstyling cosmetic having natural hairstyling properties with little stickiness, obtained by blending a water-soluble polymer, as a hairstyling resin, into a wax and a fluid oil component.

Additionally, Patent Document 2 proposes an emulsion-type hair cosmetic that allows hair to be easily arranged and that has little oiliness or stickiness, obtained by blending a vegetable-derived semi-solid oil component, candelilla wax, a liquid oil component, and a complex obtained from a surfactant and a higher fatty acid.

However, when a large quantity of a wax or a hairstyling resin is added, the hairstyling effects are improved, whereas oiliness and stiffness occur. Thus, the needs of consumers who sought natural styling were not being adequately met. Additionally, although the stickiness due to hairstyling agents has been reduced to a certain degree, the actual situation is such that, with regard to most hairstyling agents, the consumer must wipe or wash away the hairstyling agent that remains on the hands after use and a hairstyling agent that does not leave stickiness has not been realized.

RELATED ART

Patent Documents

Patent Document 1: JP H10-45546 A
Patent Document 2: JP 2009-209103 A

SUMMARY OF THE INVENTION

Problem to be Solved by the Invention

An objective of the present invention is to provide a water-in-oil emulsion cosmetic that has excellent hairstyling effects, that has a strong function of imparting moistness to the tissues to which it is applied, that has a dry feeling unlike that of a cream or a wax when taken on a finger, and that does not cause stickiness in the hands or the hair.

Means for Solving the Problem

As a result of carrying out diligent investigations towards solving the aforementioned problem, the present inventors discovered that, in a cosmetic containing a cross-linked siloxane elastomer, a solid oil component, a liquid oil component and water, by adjusting the amounts of the solid oil component and the liquid oil component to a specific ratio, hairstyling effects are obtained while suppressing the stickiness to the limit, providing a dry feeling unlike that of a cream or a wax when taken on a finger. Thus, the present invention was completed.

In other words, the present invention provides a water-in-oil emulsion cosmetic comprising:
(A) a cross-linked siloxane elastomer;
(B) a solid oil component;
(C) a liquid oil component; and
(D) 55% by mass or more of water; wherein
a blending ratio ((B)/(C)) of component (B) to component (C) is 0.25 to 1.5. Furthermore, the cosmetic according to the present invention is preferably solid or semi-solid and not in a stick form.

Effects of the Invention

By having the above-mentioned features, the present invention provides a cosmetic that exhibits an ability to moisturize the coated tissues to which it is applied, that does not produce stickiness, and that is dry to the touch. In particular, when applied to keratin tissues such as hair, it provides hairstyling effects such as improving the conformity of split hairs, sideburns and the like, and smoothing the surface of the hair, and can impart natural gloss to the hair and the like.

MODES FOR CARRYING OUT THE INVENTION

Figure 1:
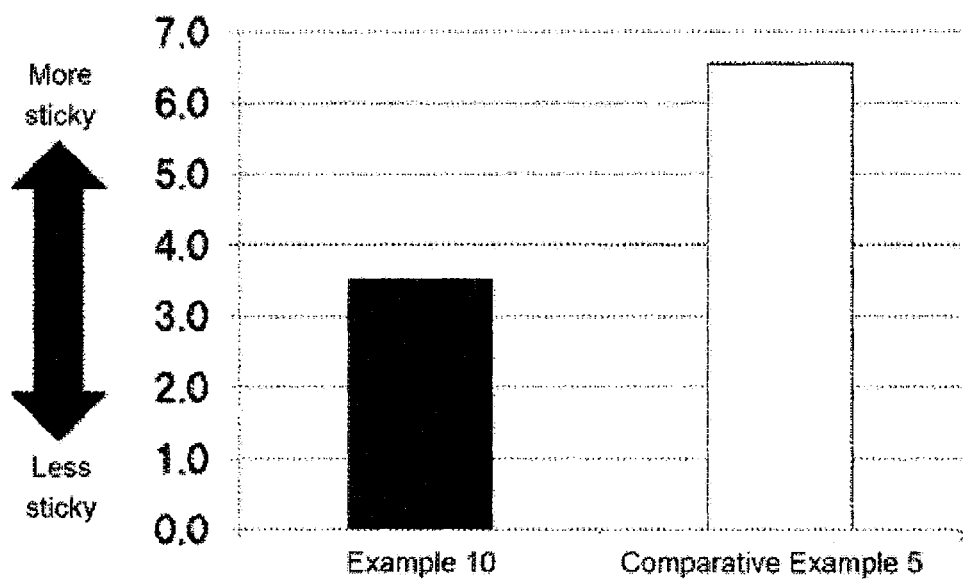
FIG. 1 A graph showing the results of rolling resistance measurements. The vertical axis represents the degree of rolling resistance, such that the greater the length on the graph, the greater the rolling resistance.

As mentioned above, the water-in-oil emulsion cosmetic of the present invention is characterized by comprising (A) a cross-linked siloxane elastomer, (B) a solid oil component, (C) a liquid oil component, and (D) water. Hereinafter, the respective components constituting the cosmetic of the present invention will be explained in detail.

<(A) Cross-Linked Siloxane Elastomer>

The (A) cross-linked siloxane elastomer (hereinafter sometimes referred to simply as "component (A)") blended into the water-in-oil emulsion cosmetic according to the present invention is a siloxane elastomer (silicone elastomer) obtained by three-dimensionally cross-linking polydimethyl siloxane, and may be emulsifying or non-emulsifying.

There is no particular limitation on the emulsifying cross-linked siloxane elastomer, but examples include cross-linked polyoxyethylene methyl polysiloxanes, alkyl group-containing cross-linked polyoxyethylene methyl polysiloxanes, cross-linked polyglycerin-modified silicones, alkyl group-containing cross-linked polyglycerin-modified silicones and the like. As these emulsifying cross-linked siloxane elastomers, it is possible to use those that are commercially available in a swollen form, in which they are swollen by various types of oil components such as silicone oils, mineral oils, triethylhexanoin and squalane. Specific examples include those mentioned below.

Examples of swollen polyoxyethylene methyl polysiloxane cross-polymers include KSG-210 (mixture of ((PEG-10/15)/dimethicone) cross-polymer and dimethicone, 20% to 30% cross-linked) (manufactured by Shin-etsu Chemical), 9011 Silicone Elastomer Blend (mixture of (PEG-12/dimethicone) cross-polymer and cyclomethicone) (manufactured by Dow Corning Toray) and the like.

Examples of swollen alkyl group-containing polyoxyethylene methyl polysiloxane cross-polymers include KSG-310 (mixture of (PEG-15/lauryl dimethicone) cross-polymer and mineral oil, 25% to 35% cross-linked), KSG-320 (mixture of (PEG-15/lauryl dimethicone) cross-polymer and isododecane, 20% to 30% cross-linked), KSG-330 (mixture of (PEG-15/lauryl dimethicone) cross-polymer and triethylhexanoin, 15% to 25% cross-linked), KSG-340 (mixture of (PEG-15/lauryl dimethicone) cross-polymer, (PEG-10/lauryl dimethicone) cross-polymer and squalane, 25% to 35% cross-linked) (all of the above manufactured by Shin-etsu Chemical) and the like.

Examples of swollen polyglycerin-modified silicone cross-polymers include KSG-710 (mixture of (dimethicone/polyglycerin-3) cross-polymer and dimethicone, 20% to 30% cross-linked) (manufactured by Shin-etsu Chemical) and the like.

Examples of swollen alkyl group-containing polyglycerin-modified silicone cross-polymers include KSG-810 (mixture of (lauryl dimethicone/polyglycerin-3) cross-polymer and mineral oil, 25% to 35% cross-linked), KSG-820 (mixture of (lauryl dimethicone/polyglycerin-3) cross-polymer and isododecane, 20% to 30% cross-linked), KSG-830 (mixture of (lauryl dimethicone/polyglycerin-3) cross-polymer and triethylhexanoin, 15% to 25% cross-linked), KSG-840 (mixture of (lauryl dimethicone/polyglycerin-3) cross-polymer and squalane, 25% to 35% cross-linked) (all of the above manufactured by Shin-etsu Chemical) and the like.

There is no particular limitation on the non-emulsifying cross-linked siloxane elastomer, but examples include methyl polysiloxane cross-polymers, methyl phenyl polysiloxane cross-polymers, vinyl dimethicone/lauryl dimethicone cross-polymers, lauryl polydimethylsiloxyethyl dimethicone/bis-vinyl dimethicone cross-polymers, alkyl ($C_{30-45}$) cetearyl dimethicone cross-polymers, cetearyl dimethicone cross-polymers and the like. As these non-emulsifying cross-linked siloxane elastomers, it is possible to use those that are commercially available in a swollen form, in which they are swollen by various types of oil components such as silicone oils, mineral oils, triethylhexanoin and squalane. Specific examples include those mentioned below.

Examples of swollen methyl polysiloxane cross-polymers include swollen dimethicone cross-polymers such as 9040 Silicone Elastomer Blend (mixture of dimethicone cross-polymer and cyclopentasiloxane, 12% cross-linked), 9041 Silicone Elastomer Blend (mixture of dimethicone cross-polymer and dimethicone 5 mPa·s, 16% cross-linked), 9045 Silicone Elastomer Blend (mixture of dimethicone cross-polymer and cyclopentasiloxane, 12.5% cross-linked) and EL-8040ID Silicone Organic Blend (mixture of dimethicone cross-polymer and isododecane, 18% cross-linked) (all of the above manufactured by Dow Corning Toray), and swollen dimethicone/vinyl dimethicone cross-polymers such as KSG-15 (mixture of (dimethicone/vinyl dimethicone) cross-polymer and cyclopentasiloxane, 4% to 10% cross-linked), KSG-16 (mixture of (dimethicone/vinyl dimethicone) cross-polymer and dimethicone 6 mPa·s, 20% to 30% cross-linked) and KSG-1610 (mixture of (dimethicone/vinyl dimethicone) cross-polymer and methyl trimethicone, 15% to 20% cross-linked) (all of the above manufactured by Shin-etsu Chemical), and the like.

Examples of swollen methyl phenyl polysiloxane cross-polymers include KSG-18A (mixture of (dimethicone/phenyl vinyl dimethicone) cross-polymer and diphenyl siloxyphenyl trimethicone, 10% to 20% cross-linked) (manufactured by Shin-etsu Chemical) and the like.

Examples of swollen vinyl dimethicone/lauryl dimethicone cross-polymers include KSG-41A (mixture of (vinyl dimethicone/lauryl dimethicone) cross-polymer and mineral oil, 20% to 30% cross-linked), KSG-42A (mixture of (vinyl dimethicone/lauryl dimethicone) cross-polymer and isododecane, 15% to 25% cross-linked), KSG-43 (mixture of (vinyl dimethicone/lauryl dimethicone) cross-polymer and triethylhexanoin, 25% to 35% cross-linked), KSG-44 (mixture of (vinyl dimethicone/lauryl dimethicone) cross-polymer and squalane, 25% to 35% cross-linked) (all of the above manufactured by Shin-etsu Chemical) and the like.

Examples of swollen lauryl polydimethylsiloxyethyl dimethicone/bis-vinyl dimethicone cross-polymers include KSG-042Z (mixture of (lauryl polydimethylsiloxyethyl dimethicone/bis-vinyl dimethicone) cross-polymer and isododecane, approximately 20% cross-linked), KSG-045Z (mixture of (lauryl polydimethylsiloxyethyl dimethicone/bis-vinyl dimethicone) cross-polymer and cyclopentasiloxane, approximately 20% cross-linked) (all of the above manufactured by Shin-etsu Chemical) and the like.

Examples of swollen alkyl ($C_{30-45}$) cetearyl dimethicone cross-polymers include VELVESIL 125 (mixture of alkyl ($C_{30-45}$) cetearyl dimethicone cross-polymer and cyclopentasiloxane, approximately 12.5% cross-linked), VELVESIL 034 (mixture of alkyl ($C_{30-45}$) cetearyl dimethicone cross-polymer and caprylyl methicone, approximately 16% cross-linked) (both of the above manufactured by Momentive Performance Materials) and the like.

Examples of swollen cetearyl dimethicone cross-polymers include VELVESIL DM (mixture of cetearyl dimethicone cross-polymer and dimethicone 5 mPa·s, approximately 17% cross-linked) (manufactured by Momentive Performance Materials) and the like.

The blended amount of component (A), relative to the total amount of the water-in-oil emulsion cosmetic, should be 0.01% to 10% by mass, preferably 0.1% to 8% by mass, more preferably 0.4% to 5% by mass, and even more preferably 0.4% to 3% by mass. If the blended amount of component (A) is less than 0.01% by mass, then stickiness occurs and when applied to the hair, an unnatural shininess occurs. If more than 10% by mass is blended, then the feeling in use becomes oily and the setting ability during hairstyling is reduced. Thus, it is not favorable for the blended amount to be in these ranges.

As component (A) in the present invention, it is possible to use one component selected from a group consisting of the above-mentioned emulsifying cross-linked siloxane elastomers and non-emulsifying cross-linked siloxane elastomers or a combination of two or more components selected therefrom. Additionally, in order to improve the dry-feeling in use, it is preferable to use a combination of one or more components selected from a group consisting of the emulsifying cross-linked siloxane elastomers and one or more components selected from a group consisting of the non-emulsifying cross-linked siloxane elastomers.

<(B) Solid Oil Component>

The (B) solid oil component (hereinafter sometimes referred to simply as "component (B)") blended into the water-in-oil emulsion cosmetic according to the present invention is an oil component that is solid at standard temperature (25° C.) and that is normally used in cosmetics. Specific examples include natural and synthetic oils and fats, hydrocarbon oils, higher fatty acids, higher alcohols and ester oils.

Examples of oils and fats include cacao butter, coconut oil, hardened coconut oil, palm oil, palm kernel oil, Japan wax kernel oil, Japan wax, hardened castor oil and the like.

Examples of hydrocarbon oils include ozokerite, ceresin, polyethylene wax, microcrystalline wax, paraffin wax and the like.

Examples of higher fatty acids include lauric acid, myristic acid, palmitic acid, stearic acid, behenic acid, 12-hydroxystearic acid, undecylenic acid and the like.

Examples of higher alcohols include linear alcohols (for example, lauryl alcohol, cetyl alcohol, stearyl alcohol, behenyl alcohol, myristyl alcohol, cetostearyl alcohol, etc.); branched alcohols (for example, monostearyl glycerin ether (batyl alcohol)) and the like.

Examples of ester oils include myristyl myristate, cetyl myristate, stearyl stearate, cetyl stearate, cetyl palmitate, cholesteryl stearate, cholesteryl oleate, dextrin palmitate, inulin stearate, hydrogenated jojoba oil and the like.

Among the above-mentioned solid oil components, one or more types selected from among hydrocarbon oils and ester oils are preferable in view of non-stickiness and spreadability by hand.

In the water-in-oil emulsion cosmetic according to the present invention, it is possible to blend in a semi-solid oil component as the above-mentioned solid oil component.

There is no particular limitation on the semi-solid oil component used in the present invention, but examples include vaseline, glyceryl trilanolate, soft lanolin fatty acid, branched or hydroxylated cholesteryl fatty acids, dipentaerythritol fatty acid esters (such as dipentaerythritol hexaoxystearate), isostearic acid-hardened castor oil, monohydroxystearic acid-hardened castor oil, tri(caprylic/capric/myristic/stearic acid) glyceride, myristyl lactate, dimer dilinoleic acid-hydrogenated castor oil, (phytosteryl/behenyl) dimer dilinoleate, (phytosteryl/isostearylketyl/stearyl/behenyl) dimer dilinoleate, phytosteryl oleate, pentaerythrityl tetra(behenate/benzoate/ethylhexanoate), dipentaerythrityl hexahydroxystearate and the like. In the cosmetic of the present invention, vaseline is preferably blended as the solid oil component in order to improve the hairstyling effects.

The blended amount of component (B), relative to the total amount of the water-in-oil emulsion cosmetic, should be 20% by mass or less, preferably 1.0% to 20% by mass. If the blended amount of component (B) is less than 1.0% by mass, then sufficient hardness as a cosmetic cannot be obtained. If more than 20% by mass is blended, then the spreadability becomes poor. Thus, it is not favorable for the blended amount to be in these ranges.

<(C) Liquid Oil Component>

The (C) liquid oil component (hereinafter sometimes referred to simply as "component (C)") blended into the water-in-oil emulsion cosmetic according to the present invention is an oil component that is liquid at standard temperature (25° C.) and that is normally used in cosmetics. Specific examples include natural and synthetic oils and fats, fatty acids, ester oils, hydrocarbon oils, higher alcohols, silicone oils and the like.

Examples of oils and fats include linseed oil, camellia oil, macadamia nut oil, corn oil, olive oil, avocado oil, sasanqua oil, castor oil, safflower oil, apricot kernel oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, tea seed oil, evening primrose oil and the like.

Examples of fatty acids include heptanoic acid, octanoic acid, nonanoic acid, decanoic acid, pentadecanoic acid, heptadecanoic acid, nonadecanoic acid, isostearic acid, oleic acid, linoleic acid, linolenic acid, arachidonic acid and the like.

Examples of ester oils include pentaerythritol tetraoctanoate, cetyl octanoate, hexyl laurate, isopropyl myristate, octyldodecyl myristate, octyl palmitate, isopropyl isostearate, octyl isopalmitate, isodecyl oleate, cetyl ethylhexanoate, glyceryl tri-2-ethylhexanoate and the like.

Examples of hydrocarbon oils include liquid paraffin, squalane, squalene, paraffin, isoparaffin, octane, decane, dodecane, isododecane, hexadecane, isohexadecane and the like.

Examples of higher alcohols include octyl alcohol, isostearyl alcohol, oleyl alcohol and the like.

Examples of silicone oils include chained silicones such as dimethyl polysiloxane, methylphenyl polysiloxane and methylhydrogen polysiloxane, cyclic silicones such as octamethyl cyclotetrasiloxane, decamethyl cyclopentasiloxane, dodecamethyl cyclohexasiloxane and diphenylsiloxyphenyl trimethicone, and the like.

The blended amount of component (C), relative to the total amount of the water-in-oil emulsion cosmetic, should be 1.0% to 40% by mass, preferably 3.0% to 30% by mass and more preferably 5.0% to 25% by mass. If the blended amount of component (C) is less than 1.0% by mass, then the spreadability at the tune of application is poor. If more than 40% by mass is blended, then stickiness occurs and when applied to the hair, an unnatural shininess occurs. Thus, it is not favorable for the blended amount to be in these ranges.

In order to suppress stickiness and improve spreadability in the water-in-oil emulsion cosmetic according to the present invention, the blending ratio ((B)/(C)) between the (B) solid oil component and the (C) liquid oil component should be 0.25 to 1.5 in terms of the ratio by mass, more preferably 0.5 to 1.2. If the blending proportion of component (B) is high, stickiness occurs and the spreadability becomes poor. Additionally, if the blending proportion of component (C) is high, the hairstyling effects become weaker.

The water-in-oil emulsion cosmetic according to the present invention further contains (D) water (hereinafter sometimes referred to simply as "component (D)") as an essential component.

The blended amount of component (D) is 55% by mass or more relative to the total amount of the water-in-oil emulsion cosmetic. If the water content is less than 55% by mass, then there is a tendency for stickiness to occur and for the hairstyling effects on hair and the like to become worse.

The cosmetic of the present invention may contain, in addition to the above-mentioned essential components (A) to (D), other optional components that may be blended into cosmetics, within a range in which the effects of the present invention are not lost. Examples of optional components include those indicated below.

By blending in an (E) surfactant, the emulsion stability can be improved. The (E) surfactant to be blended into the cosmetic according to the present invention is a surfactant that is normally used when manufacturing a water-in-oil emulsion, and there is no particular limitation thereon, but examples include non-ionic surfactants, silicone-based surfactants and the like having an HLB of 8 or lower. Among these, it is preferably to use silicone-based surfactants in view of the lack of stickiness and the lightness. Silicone-based surfactants refer to polyether-modified silicones that have polyoxyalkylene structures introduced on a silicone skeleton, and that are not cross-linked.

Specific examples of silicone-based surfactants include polyether-modified silicones such as PEG-10 dimethicone, PEG-9 polydimethylsiloxyethyl dimethicone and lauryl PEG-9 polydimethylsiloxyethyl dimethicone. These may be blended as one type or by mixing two or more types.

Additionally, the silicone-based surfactant may be blended in the state of a silicone gel consisting of that surfactant and a solvent, and a commercially available silicone gel may be used. Examples include KF-6017, KF-6028, KF-6038 (all of the above manufactured by Shin-etsu Chemical) and the like. Oil components that are contained, as solvents, in these silicone gels are also classified as the above-mentioned component (C), and it goes without saying that the blended amounts thereof are included in the blended amount of component (C).

The blended amount of the (E) surfactant in the cosmetic of the present invention should normally be 0.05% to 20% by mass, preferably 0.1% to 10% by mass and more preferably 0.5% to 5% by mass.

By blending in a (F) humectant, it is possible to improve the moisture retention in the tissue (hair, skin or the like) after the cosmetic has been applied.

Specific examples of humectants include glycols such as propylene glycol, dipropylene glycol, 1,3-butylene glycol, 1,4-butylene glycol, diethylene glycol, triethylene glycol and polyethylene glycol; glycerins such as glycerin, diglycerin and polyglycerin; sugar alcohols such as sorbitol, mannitol, maltitol, xylitol and erythritol; sugars such as fructose, glucose, galactose, maltose, lactose and trehalose; and the like.

When blending a humectant into the cosmetic of the present invention, the blended amount thereof should normally be 0.1% to 50% by mass, preferably 1% to 30% by mass, and more preferably 5% to 20% by mass.

Examples of optional components other than those mentioned above include thickeners, ceramides, vitamins, UV absorbers, chelating agents, anti-bacterial agents, preservatives, vegetable extracts, amino acids, various types of medicinal agents, lower alcohols such as ethanol, and the like.

The cosmetic of the present invention can be produced in accordance with conventionally used methods. Stated simply, it may be produced by separately mixing the oil-based components and the water-based components while heating as needed, emulsifying the water phase in the oil phase, and then filling a container with the resulting emulsion, and gradually cooling the emulsion.

The cosmetic of the present invention comprises a large amount of water, and can therefore impart moisture to tissues (hair, skin and the like) to which it is applied. Additionally, it has a characteristic hardness obtained by adjusting the blended amounts of the solid oil component and the liquid oil component to a specific ratio. Thus, there is little sense of stickiness, and when applied to the skin, the emulsion breaks down and the water in the internal phase is released, thereby resulting in a watery texture. Furthermore, a dry texture is obtained by blending a siloxane elastomer.

The hardness of the cosmetic of the present invention is preferably 50 to 500, more preferably 75 to 450, and even more preferably 100 to 400. In this case, "hardness" refers to the value obtained by measuring the cosmetic after being placed, the day after manufacture, for three hours in a 25° C. constant-temperature chamber, using a rheometer (COMPAC 100-II, manufactured by SUN) with a load of 200 g, an 84 pressure-sensing shaft, a needle insertion depth of 10.0 mm and a needle insertion speed of 300 mm/min.

The cosmetic of the present invention is a solid or semi-solid cosmetic that is contained, for example, in a wide-mouthed container or the like. The cosmetic of the present invention does not include cosmetics in a stick form. Additionally, the cosmetic of the present invention is preferably used by being taken and applied by the hands and fingers. When taking the cosmetic in the hands and fingers, the cosmetic can be taken directly using a finger from the container or using a tool such as a spatula.

The cosmetic of the present invention is also known as a balm base and may be used to care for the entire body, and since it has good spreadability and has hairstyling effects, it is preferably used for keratin tissue care and hairstyling. Additionally, the cosmetic of the present invention is not sticky, so there is no need to wipe or wash away the cosmetic remaining on the hands and fingers after use, even when used as a hairstyling cosmetic.

Examples

The present invention will be explained in further detail by providing examples below, but the present invention is not in any way limited to these examples. The blended amounts are in percentage by mass where not noted otherwise.

Water-in-oil emulsion cosmetics having the compositions indicated in Table 1 below were prepared by separately mixing the oil-based components and the water-based components included in the compositions of each example while heating the mixtures, emulsifying the water phase in the oil phase, and then filling a container with the resulting emulsion, and gradually cooling the emulsion. The following tests were performed on the prepared cosmetics.

1. Effects Test

Actual texture tests were performed by ten expert panelists. The usage property categories were non-stickiness in hands and hair, spreadability by hand, arrangeability (ease of preparation of hairstyle) and setting ability (retention of hairstyle), each of the categories being evaluated on the basis of the following criteria. The results are shown in the table.

<Evaluation Criteria>

A: Nine or more panelists replied that the effects were excellent.

B: Seven or eight panelists replied that the effects were excellent.

C: Three to six panelists replied that the effects were excellent.

D: Two or fewer panelists replied that the effects were excellent.

TABLE 1

|  |  | Ex. 1 | Ex. 2 | Ex. 3 | Ex. 4 | Ex. 5 | Ex. 6 | Ex. 7 | Ex. 8 |
|---|---|---|---|---|---|---|---|---|---|
| Cross-linked siloxane elastomer | (dimethicone/phenylvinyl dimethicone) cross-polymer | 0.7 | 0.7 | 0.7 | 0.7 | 0.7 | 0.7 | 0.7 | 0.7 |
|  | (dimethicone/(PEG-10/15)) cross-polymer | 0.4 | 0.4 | 0.4 | 0.4 | 0.4 | 0.4 | 0.4 | 0.4 |
| Solid oil component | paraffin wax | 4.6 | 4.6 | 4.6 | 6.4 | 6.4 | 9.2 | 11 | — |
|  | microcrystalline wax | — | — | — | — | — | — | — | 4 |
|  | polyethylene wax | 0.4 | 0.4 | 0.4 | 0.6 | 0.6 | 0.8 | 1 | 1 |
|  | candelilla wax | — | — | — | — | — | — | — | — |
|  | rice bran wax | — | — | — | — | — | — | — | — |
|  | myristyl myristate | 1 | 1 | 3 | 3 | 3 | 3 | 3 | 3 |
| Semi-solid oil component | vaseline | — | — | — | — | 3 | 3 | 3 | — |
| liquid oil component | decamethyl cyclopentasiloxane | 15 | — | — | — | — | — | — | — |
|  | isododecane | — | 10 | 10 | 10 | 10 | 10 | 10 | 10 |
|  | glyceryl tri-2-ethylhexanoate | 2 | — | — | — | — | — | — | — |
|  | methyl polysiloxane | 3 | 4 | 4 | 4 | 4 | 3 | 2 | 4 |
|  | diphenylsiloxyphenyl trimethicone | 3 | — | — | — | — | — | — | — |
|  | water | 56.7 | 65.7 | 63.7 | 61.7 | 58.7 | 56.7 | 55.7 | 63.7 |
|  | glycerin | 6 | 6 | 6 | 6 | 6 | 6 | 6 | 6 |
|  | 1,3-butylene glycol | 6 | 6 | 6 | 6 | 6 | 6 | 6 | 6 |
|  | PEG10-dimethicone | 1 | 1 | 1 | 1 | 1 | 1 | 1 | 1 |
|  | EDTA-2Na | 0.1 | 0.1 | 0.1 | 0.1 | 0.1 | 0.1 | 0.1 | 0.1 |
|  | methylparaben | 0.1 | 0.1 | 0.1 | 0.1 | 0.1 | 0.1 | 0.1 | 0.1 |
|  | Total | 100 | 100 | 100 | 100 | 100 | 100 | 100 | 100 |
|  | semi-solid and solid oil components/liquid oil components | 0.26 | 0.43 | 0.57 | 0.71 | 0.93 | 1.23 | 1.5 | 0.57 |
|  | water content | 56.7 | 65.7 | 63.7 | 61.7 | 58.7 | 56.7 | 55.7 | 63.7 |
| Evaluation | non-stickiness | A | A | A | A | A | B | A | A |
|  | spreadability by hand | A | A | A | A | A | B | B | A |
|  | arrangeability | B | B | B | B | A | A | A | B |
|  | setting ability | B | B | B | A | A | A | A | B |

|  |  | Ex. 9 | Ex. 10 | Comp. Ex. 1 | Comp. Ex. 2 | Comp. Ex. 3 | Comp. Ex. 4 |
|---|---|---|---|---|---|---|---|
| Cross-linked siloxane elastomer | (dimethicone/phenylvinyl dimethicone) cross-polymer | 0.7 | 0.7 | 0.7 | 0.7 | 0.7 | 0.7 |
|  | (dimethicone/(PEG-10/15)) cross-polymer | 0.4 | 0.08 | 0.4 | 0.8 | 0.4 | 0.4 |
| Solid oil component | paraffin wax | — | 6.4 | 5.5 | 11 | 1.8 | 11 |
|  | microcrystalline wax | — | — | — | — | — | — |
|  | polyethylene wax | 5 | 0.6 | 0.5 | 1 | 0.2 | 1 |
|  | candelilla wax | — | — | — | — | — | — |
|  | rice bran wax | — | — | — | — | — | 5 |
|  | myristyl myristate | 3 | 3 | 3 | 3 | 1 | 3 |
| Semi-solid oil component | vaseline | — | 3 | 3 | 3 | — | — |
| liquid oil component | decamethyl cyclopentasiloxane | — | — | — | — | — | — |
|  | isododecane | 10 | 10 | 15 | 5 | 10 | 10 |
|  | glyceryl tri-2-ethylhexanoate | — | — | — | — | — | — |
|  | methyl polysiloxane | 4 | 4 | 8 | 4 | 4 | 4 |
|  | diphenylsiloxyphenyl trimethicone | — | — | — | — | — | — |
|  | water | 63.7 | 58.52 | 50.7 | 58.3 | 68.7 | 51.7 |
|  | glycerin | 6 | 6 | 6 | 6 | 6 | 6 |
|  | 1,3-butylene glycol | 6 | 6 | 6 | 6 | 6 | 6 |
|  | PEG10-dimethicone | 1 | 1.5 | 1 | 1 | 1 | 1 |
|  | EDTA-2Na | 0.1 | 0.1 | 0.1 | 0.1 | 0.1 | 0.1 |
|  | methylparaben | 0.1 | 0.1 | 0.1 | 0.1 | 0.1 | 0.1 |
|  | Total | 100 | 100 | 100 | 100 | 100 | 100 |
|  | semi-solid and solid oil components/liquid oil components | 0.57 | 0.93 | 0.52 | 2 | 0.21 | 1.43 |
|  | water content | 63.7 | 58.52 | 50.7 | 58.3 | 68.7 | 51.7 |
| Evaluation | non-stickiness | A | A | C | D | A | D |
|  | spreadability by hand | A | A | B | D | A | B |
|  | arrangeability | B | A | D | C | D | B |
|  | setting ability | B | A | D | A | D | B |

When the blended amount of water was less than 55% by mass (Comparative Example 1 and Comparative Example 4), a tendency for stickiness to occur and for the arrangeability (ease of setting of hairstyle) and setting ability (holding of hairstyle) to be worse was observed. When the blending proportion of the solid oil component was made high (component (B)/component (C)=2.0, Comparative Example 2), the setting ability was good, but the arrangeability was poor, the cosmetic was difficult to spread, and stickiness occurred. Conversely, when the blending proportion of the solid oil component was made low (component (B)/component (C)=0.21, Comparative Example 3), the cosmetic was easy to spread and there was no stickiness, but both the arrangeability and the setting ability were worse.

In contrast to the above-mentioned comparative examples, when the essential components of the present invention were blended and the blending ratio between the solid oil component and the liquid oil component was 0.25 to 1.5, cosmetics having sufficient hairstyling performance and also performing well in terms of spreadability and stickiness were obtained in all cases.

2. Stickiness (Rolling Resistance) when Dried after Application

Next, a hair wax comprising the composition indicated below was prepared by heating and melting (2) to (10) to form an oil phase; adding (12), (13) and (15) to (11), and after stirring and dissolving the added components, adding (1) and homogeneously dispersing this mixture to obtain a water phase; adding the oil phase to the water phase and emulsifying the mixture, then adding (14) and (16). The hair wax prepared in this way was measured, as Comparative Example 5, together with the aforementioned Example 10, for the rolling resistance, according to the method described below, and stickiness evaluations were compared.

|  | Comparative Example 5 (Hair wax) | % by mass |
|---|---|---|
| (1) | Kaolin | 2.0 |
| (2) | Phenylmethyl polysiloxane | 5.0 |
| (3) | Amodimethicone | 1.0 |
| (4) | Candelilla wax | 18.0 |
| (5) | Phytosteryl ricinoleate | 5.0 |
| (6) | Hydroxystearic acid-hydrogenated castor oil | 3.0 |
| (7) | Decyl oleate | 5.0 |
| (8) | Methyl cyclopolysiloxane | 5.0 |
| (9) | Octamethyl trisiloxane | 3.0 |
| (10) | Isostearic acid | 3.0 |
| (11) | Ion-exchanged water | balance |
| (12) | 1,3-Butylene glycol | 5.0 |
| (13) | 2-Undecyl-N,N,N-(hydroxyethylcarboxymethyl)-2-imidazoline sodium salt (actual part 30%) | 8.0 |
| (14) | Xanthan gum | 1.0 |
| (15) | EDTA-2Na•2H$_2$O | 0.05 |
| (16) | Phenoxyethanol | 0.5 |

Samples of the aforementioned Example 10 and Comparative Example 5 were measured for stickiness when dry by measuring the rolling resistance between a sample and a probe using the apparatus described in Japanese Patent No. 3945729. The measurement conditions were set so that the sliding speed was 1.2 cm/s, the sliding stroke was 20 mm, the sample amount was 20 µL, the stage temperature was 32° C., the room temperature was 25° C. and the relative humidity was 50%. The results are shown in FIG. 1 and FIG. 2.

As is clear from the results in FIG. 1, it was confirmed that the sample in Example 10 had lower rolling resistance and less stickiness when dry than the sample in Comparative Example 5. In FIG. 1, the vertical axis represents the rolling resistance, such that the greater the length on the graph, the greater the rolling resistance.

Figure 2:
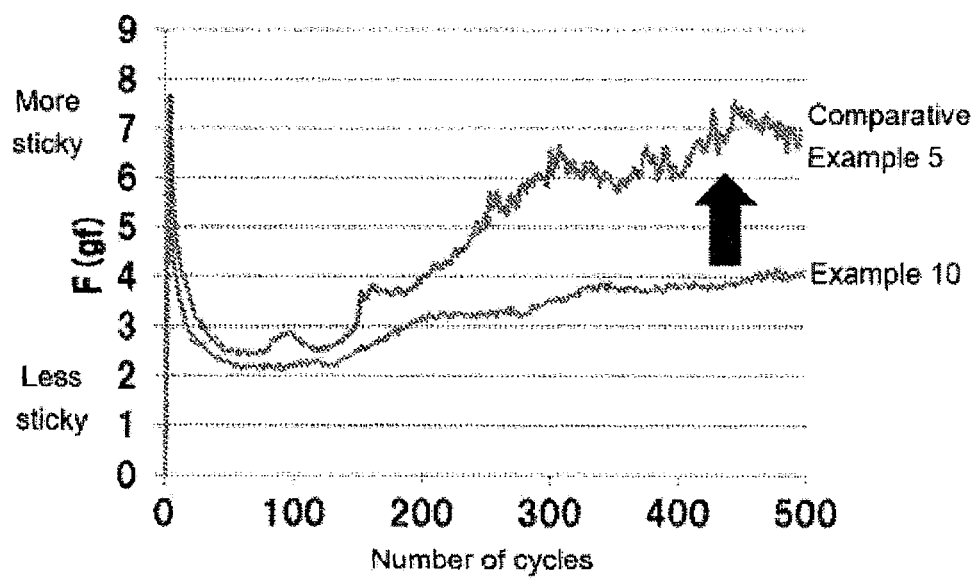
FIG. 2 A graph showing the degree of rolling resistance together with the increase in number of sliding cycles. The vertical axis represents the degree of rolling resistance, such that the greater the length on the graph, the greater the rolling resistance.

Additionally, as is clear from the results in FIG. 2, the sample in Comparative Example 5 became much stickier along with increasing the number of sliding cycles, whereas the increase in stickiness of the sample in Example 10 was gradual and the stickiness thereof is lesser than the sample in comparison to Comparative Example 5. This shows that stickiness did not tend to occur as the sample in Example 10 became dry.

The invention claimed is:

1. A water-in-oil emulsion, cosmetic comprising:
   (A) a cross-linked siloxane elastomer obtained by three-dimensionally crosslinking a siloxane elastomer;
      wherein said component (A) further comprises one or more emulsifying cross-linked siloxane elastomers in combination with one or more non-emulsifying cross-linked siloxane elastomers;
   (B) a solid oil component;
      wherein said component (B) further comprises a semi-solid component;
   (C) a liquid oil component; and
   (D) 55% by mass or more of water, relative to the total mass of the water-in-oil emulsion cosmetic;
   wherein a blending ratio ((B)/(C)) between component (B) and component (C) is 0.25 to 1.5.

2. The water-in-oil emulsion, cosmetic according to claim 1, wherein:
   a blended amount of said (B) solid oil component is 20% by mass or less relative to said water-in-oil emulsion cosmetic.

3. The water-in-oil emulsion cosmetic, according to claim 1, wherein:
   said component (B) is at least one oil component selected from the group consisting of hydrocarbon oils and ester oils.

4. The water-in-oil emulsion cosmetic, according to claim 1, wherein:
   said water-in-oil cosmetic is made of at least one form selected from the group consisting of a solid form and a semi-solid form and is not made of a stick form.

5. The water-in-oil emulsion cosmetic, according to claim 1, wherein:
   said water-in-oil cosmetic is applicable in a keratin tissue care product.

* * * * *